United States Patent [19] [11] 4,237,043
Korbanka et al. [45] Dec. 2, 1980

[54] ORGANOTIN COMPOUNDS, THE PREPARATION AND USE THEREOF

[75] Inventors: Helmut Korbanka, Adelsried; Franz Scheidl, Gersthofen, both of Fed. Rep. of Germany

[73] Assignee: Hoechst Aktiengesellschaft, Frankfurt am Main, Fed. Rep. of Germany

[21] Appl. No.: 931,897

[22] Filed: Aug. 8, 1978

[30] Foreign Application Priority Data

Aug. 9, 1977 [DE] Fed. Rep. of Germany ....... 2735810

[51] Int. Cl.$^3$ ............................................. C07F 7/22
[52] U.S. Cl. ..................... 260/45.75 S; 260/45.75 H; 260/45.75 T; 260/429.7
[58] Field of Search ............... 260/429.7, 45.75 S, 260/45.75 H, 45.75 T

[56] References Cited

U.S. PATENT DOCUMENTS

| | | | |
|---|---|---|---|
| 3,440,255 | 4/1969 | Matsuda et al. | 260/429.7 |
| 4,080,362 | 3/1978 | Hutton et al. | 260/429.7 X |
| 4,080,363 | 3/1978 | Hutton et al. | 260/429.7 X |
| 4,105,684 | 8/1978 | Hutton et al. | 260/429.7 |

*Primary Examiner*—Helen M. S. Sneed
*Attorney, Agent, or Firm*—Connolly and Hutz

[57] ABSTRACT

The invention provides novel organotin compounds and their preparation by reaction of organotin halides with mercaptans, thiocarboxylic acid esters, carboxylic acids or carboxylic acid partial esters. Suitable organotin halides are those obtained by reaction of Sn+HCl with an olefin which carries a carbonyl group in adjacent position to the olefinic double bond and which is substituted in addition by at least one carboxylate group not adjacent to the double bond.

The novel compounds are used as starting for stabilizing halogen-containing polymers without influencing their transparency.

5 Claims, No Drawings

ORGANOTIN COMPOUNDS, THE PREPARATION AND USE THEREOF

This invention relates to novel organotin compounds, a process for their preparation, and their use as stabilizers for halogen-containing polymers.

When processing halogen-containing polymers, especially polymers and copolymers of vinyl chloride and vinylidene chloride, heat stabilizers have to be added to prevent or substantially retard decomposition resulting in discoloration, brittleness and general deterioration of the mechanical properties.

Generally lead salts of organic and/or inorganic acids, barium, cadmium, calcium, strontium, zinc and other metal salts of organic acids or other H-acidic compounds, for example phenols and acidic esters, and organotin compounds are used as heat stabilizers. Among the most active heat stabilizers are organotin compounds such as organotin mercaptides, thioglycolates and carboxylates.

It has now been found that mixtures of hitherto unknown organotin compounds having the formulae

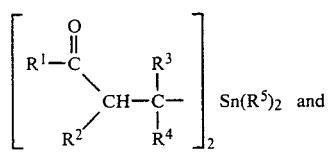

I

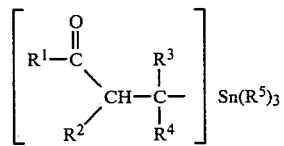

II in which the symbols used have the following meanings, are excellently suitable as heat stabilizers for halogen-containing polymers.

The symbols in the formulae have the following meanings:

$R^1$ is OH, —$NH_2$, an alkylamino or arylamino radical, an O-alkyl or O-aryl radical, both the latter radicals being unsubstituted or substituted by aryl or alkyl and optionally carrying as additional substituents halogen or a hydroxy, thioether, ether and/or carboxyl group;

$R^2$ to $R^4$, being identical or different, each are
(a) 0 to 2 hydrogen atoms, or
(b) alkyl radicals having from 1 to 30 carbon atoms, with the proviso that at least one of these radicals is a

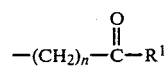

group, where $R^1$ is as defined above and n an integer of from 1 to 15;

$R^5$ is —S—$(CH_2)_m$—$CO_2$—alkyl, —S—alkyl, —$O_2$C—alkyl or —$O_2$C—CH=CH—$CO_2$—alkyl, m being 1 or 2 and the alkyl radical optionally containing —O—, —S— or —$CO_2$ groups and OH substituents.

The radicals $R^1$ to $R^5$ corresponding to one another in the components I and II of the mixture are always identical.

Examples of $R^1$ are OH, $NH_2$, alkyl- or arylamino radicals such as

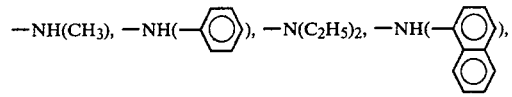

O-alkyl radicals such as —$OCH_3$, —$OC_2H_5$, —$OC_8H_{17}$,

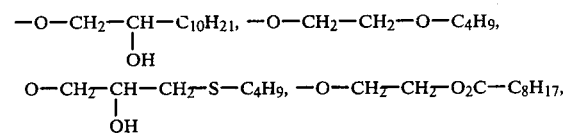

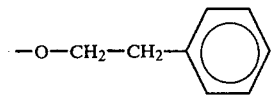

and O-aryl radicals such as

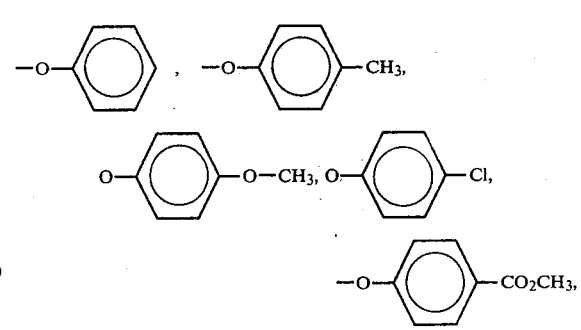

Examples of $R^2$ to $R^4$ are at least one radical

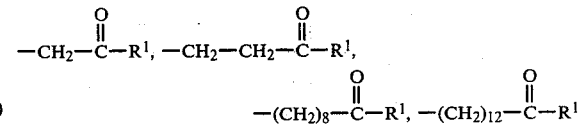

where $R^1$ is as defined above, furthermore H, methyl, ethyl, propyl, hexyl, dodecyl, octadecyl etc.

Examples of $R^5$ are known radicals constantly used in tin stabilizer chemistry, for example from the mercaptide series: —S—$C_8H_{17}$, —S—$C_{12}H_{25}$, —S—$C_{18}H_{25}$, from the alkylthiocarboxylate series for example —S—$(CH_2)_n$—$CO_2$—alkyl (n=1 and 2; alkyl=octyl, lauryl, ocatdecyl, 2-hydroxy-octadecyl etc.), from the carboxylate series for example

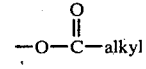

(alkyl=heptyl, undecyl, heptadecyl etc.) and from the partial ester series for example

(alkyl=methyl, butyl, octyl, dodecyl etc.).

Further known examples for radicals R⁵ are described in German Offenlegungsschriften Nos. 1 418 001; 1 418 017; 1 418 019; 1 494 332; 1 544 729; 1 569 070; 1 569 136; 1 569 170; 1 694 936; 1 801 274 and 2 006 711, in British Pat. No. 1,439,752 and U.S. Pat. No. 3,925,309.

The novel organotin compounds are obtained according to processes known from organotin chemistry. Starting products are organotin halide mixtures of the formulae

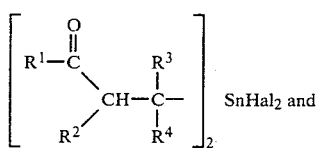

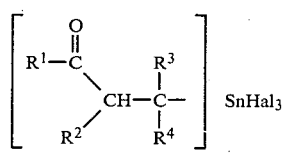

the symbols R¹ to R⁴ are as defined above; Hal is Cl, Br, I-which, in accordance with the indications of our co-pending application Ser. No. 931,678 filed Aug. 7, 1978 are obtained by reaction of defined substituted olefins with metallic tin and hydrogen chloride. These mixtures are reacted with mercaptans, thiocarboxylic acid esters, carboxylic acids and partial esters such as maleic acid monoesters, at temperatures of from about 0° to 150°, preferably 15° to 80° C., in the presence of hydrogen halide acceptors such as NaOH, NaHCO₃, or amines such as triethylamine, pyridine etc., and optionally in the presence of inert solvents such as ethers, ketones, esters, aliphatic or aromatic hydrocarbons. It is furthermore possible to hydrolyze the organotin halides to organotin oxides and to react the latter ones with the —SH or —CO₂H compounds with splitting-off of water.

Preferred organotin halides are those of the above formulae, where R¹ is O-alkyl having from 1 to 30, preferably 1 to 20, and especially 1 to 10, carbon atoms, R³ and R⁴ each are hydrogen and R² is

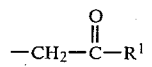

where R¹ has the above preferred meaning.

Preferred reactants which stand for the radical R⁵ in the products of the invention are esters of thioglycolic or thiopropionic acid, alkylmercaptans having preferably from 8 to 18 carbon atoms such as octyl-, dodecyl- or stearyl- mercaptan, fatty acids having from 8 to 34 carbon atoms, for example lauric, 2-ethylhexanoic, stearic, montanic acid, or maleic acid monoester.

Since the organotin halides used are mixtures of tri- and dihalides (ratio organotin dichloride/organotin trichloride from 1:0.01 to 1:4 depending on the preparation conditions), the organotin compounds of the invention are mixtures, too, which, however, it not disadvantageous for the intended application. For, it is known from the practice of organotin stabilizers that mixtures of dialkyl- and monoalkyltin stabilizers have a synergistic stabilizing effect in chlorine-containing polymers such as polyvinyl chloride. If desired, the pure di- or monoorganotin stabilizers of the formulae I and II, respectively, can of course be obtained alternatively; in this case, however, the starting products are the pure di- or trihalides which can be isolated from the mixtures according to known methods (for example fractional crystallization).

Some typical representatives of the organotin compounds of the invention are stated as follows without, however, limiting the invention to these substances: mixture of di- and mono-(bis-2,3-carbomethoxy-)propyl-tin-di- and -trioctylthioglycolate

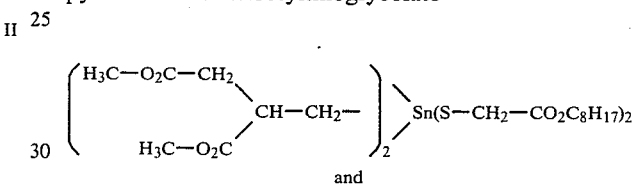

and

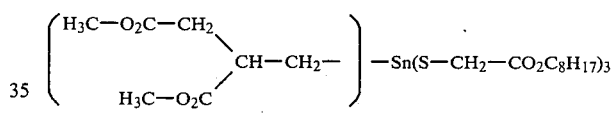

mixture of di- and mono-(bis-2,4-carbobutoxy-)butyl-tin-di- and tri-n-dodecylmercaptide

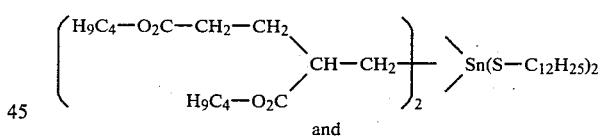

and

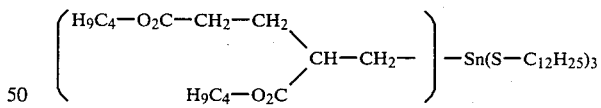

mixture of di- and mono-(bis-2,3-carbophenoxy-)propyl-tin-di- and -trilaurate

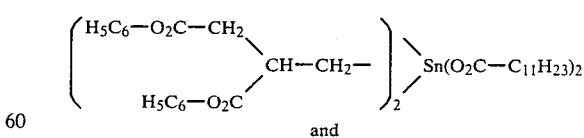

and

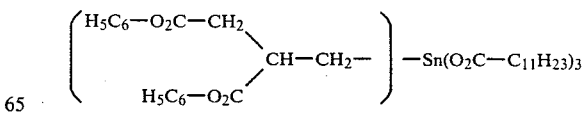

mixture of di- and mono-(bis-2,3-carbo-2-hydroxy-tetradecoxy-)propyl-tin-di- and -trimonobutylmaleate

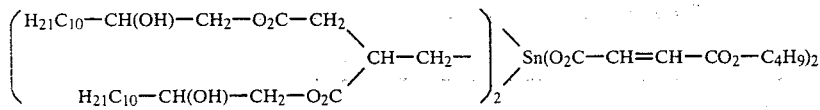

and

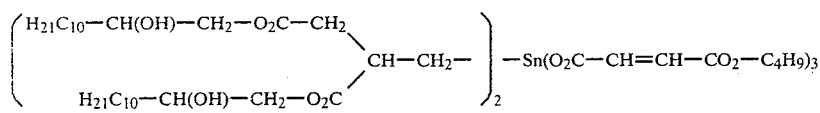

mixture of di- and mono-(bis-2,3-anilino-carbonyl)propyltin-di- and tributylthiopropionate

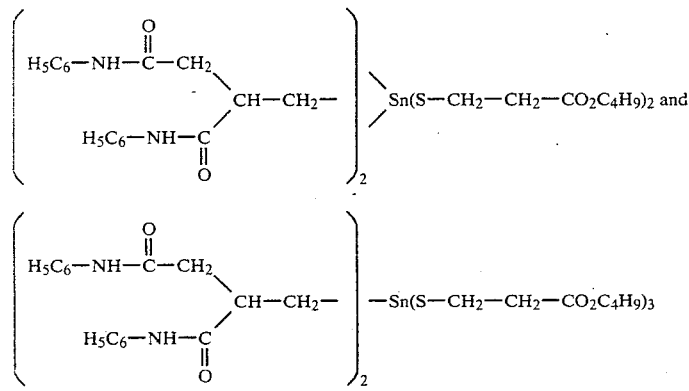

The organotin stabilizers of the invention have a very good stabilizing action in halogen-containing polymers, for example chloropolyethylene, hard or soft polyvinyl chloride, polyvinylidene chloride, polyvinyl chloroacetate or vinylchloride/alpha-olefin copolymers, which action corresponds to that of known compounds, for example dibutyltin stabilizers. Moreover, it has been observed that thermoplastic compositions stabilized with the novel compounds have an improved transparency.

Generally, the novel stabilizers are used together with other known stabilizers such as calcium stearate or other stabilizing metal salts, stabilizing auxiliaries (epoxides, organo-phosphites), antioxidants such as phenols, UV stabilizing compounds, lubricants, plasticizers, pigments, fillers, auxiliaries and the like. They are used in amounts of from 0.1 to 10, preferably 0.2 to 5, and especially 0.5 to 3, parts by weight, relative to 100 parts by weight of polymer.

The following Examples illustrate the invention. Examples 1 to 10 described the preparation of the novel organotin compounds, Examples 11 to 32 show the polyvinyl chloride-stabilizing action as compared to known organotin compounds.

EXAMPLE 1

40.8 g (0.2 mol) thioglycolic acid-2-ethylhexyl ester, 36.0 g (0.2 chlorine equivalent) of a mixture of about 59 weight % di(bis-2,3-carbomethoxy)-propyltin dichloride and about 41 weight % mono(bis-2,3-carbomethoxy)-propyltin trichloride (chlorine content of the mixture: 19.7%, tin content: 21.8%) and 300 ml toluene were introduced into a three-necked flask having a capacity of 500 ml provided with agitator, inside thermometer and dropping funnel. At 20° C., a solution of 20.2 g (0.2 mol) triethylamine in 50 ml toluene was added dropwise. Subsequently, agitation was continued for 2 hours at room temperature. The precipitate formed (27.5 g triethylammonium chloride) was then suction-filtered. After having distilled off the toluene, the organotin stabilizer was isolated from the filtrate in the form of a yellowish liquid.

Yield: 69.5 g organotin-2-ethylhexylthioglycolate.
Analysis:
11.3% Sn
0.1% Cl.

EXAMPLES 2 to 10

According to the operation mode of Example 1, a number of further organotin stabilizers was prepared with the use of the reactants listed in the following Table 1. In all cases, 0.2 equivalent of the organotin halide, 0.2 mol of the reaction component, 0.2 mol of triethylamine as hydrogen chloride acceptor and a total of 350 ml of toluene as solvent was used. About 27.5 g of triethylamine hydrochloride were isolated as residue in all cases. As in Example 1, the organotin compounds obtained did practically not contain any chlorine. In Table 2, the results are indicated in detail, Table 1 gives a survey on the starting materials and their amounts.

TABLE 1

| Ex. No. | Mixture of %(R)₂SnCl₂ | %(R)SnCl₃ | Organotin halide Structure of R | % Cl/% Sn | Amount (g) | Reaction component |
|---|---|---|---|---|---|---|
| 2 | 72 | 28 | $H_3C-O_2C-CH_2$\\$\quad\quad\quad\quad\quad\quad$ CH—CH₂—\\$H_3C-O_2C$/ | 17.8/23.0 | 39.9 | (1) |
| 3 | 87 | 13 | $n\text{-}H_9C_4-O_2C-CH_2$\\$\quad\quad\quad\quad\quad\quad\quad$ CH—CH₂—\\$n\text{-}H_9C_4-O_2C$/ | 13.7/16.8 | 51.8 | (2) |
| 4 | 75 | 25 | $n\text{-}H_{17}C_8-O_2C-CH_2$\\$\quad\quad\quad\quad\quad\quad\quad\quad$ CH—CH₂—\\$n\text{-}H_{17}C_8-O_2C$/ | 10.4/12.7 | 68.3 | (3) |
| 5 | 50 | 50 | Ph—$O_2C-CH_2$\\$\quad\quad\quad\quad\quad\quad$ CH—CH₂—\\Ph—$O_2C$/ | 15.2/19.5 | 46.8 | (1) |
| 6 | 68 | 32 | Ph—NH—C(=O)—$CH_2$\\$\quad\quad\quad\quad\quad\quad\quad\quad$ CH—CH₂—\\Ph—NH—C(=O)/ | 12.5/14.1 | 56.8 | (4) |
| 7 | 73 | 7 | $H_9C_4-O_2C-CH_2-CH_2$\\$\quad\quad\quad\quad\quad\quad\quad\quad\quad$ CH—CH₂—\\$H_9C_4O_2C$/ | 12.5/16.3 | 56.8 | (5) |
| 8 | 60 | 40 | $n\text{-}C_7H_{15}-CH(OH)-CH_2-O_2C-CH_2$\\$\quad\quad\quad\quad\quad\quad\quad\quad\quad\quad\quad\quad$ CH—CH₂—\\$n\text{-}C_7H_{15}-CH(OH)-CH_2-O_2C$/ | 10.8/14.3 | 65.7 | (5) |
| 9 | 55 | 45 | $n\text{-}H_9C_4-O-CH_2-CH_2-O_2C-CH_2$\\$\quad\quad\quad\quad\quad\quad\quad\quad\quad\quad\quad\quad$ CH—CH₂—\\$n\text{-}H_9C_4-O-CH_2-CH_2-O_2C$/ | 13.1/17.2 | 54.3 | (1) |
| 10 | 67 | 33 | Ph—$CO_2-CH_2-CH_2-O_2C-CH_2$\\$\quad\quad\quad\quad\quad\quad\quad\quad\quad\quad\quad\quad$ CH—CH₂—\\Ph—$CO_2-CH_2-CH_2-O_2C$/ | 11.0/13.7 | 64.5 | (1) |

(1) thioglycolic acid-2-ethylhexyl ester
(2) 3-thiopropionic acid-2-ethylhexyl ester
(3) n-dodecylmercaptan
(4) lauric acid
(5) maleic acid-mono-n-butyl ester

TABLE 2

| Example No. | Yield (g) | Content of tin (%) | to be defined as Organotin - .... |
|---|---|---|---|
| 2 | 73.2 | 10.5 | -2-ethylhexylthioglycolate |
| 3 | 88.1 | 9.8 | -2-ethylhexylthiopropionate |
| 4 | 101.1 | 8.6 | -n-dodecylmercaptide |
| 5 | 80.1 | 11.4 | -2-ethylhexylthioglycolate |
| 6 | 89.7 | 8.9 | -laurate |
| 7 | 83.5 | 11.0 | -mono-n-butylmaleate |
| 8 | 92.8 | 10.0 | -mono-n-butylmaleate |
| 9 | 87.7 | 10.6 | -2-ethylhexylthioglycolate |
| 10 | 98.1 | 9.0 | -2-ethylhexylthioglycolate |

EXAMPLES 11 to 32

These Examples show the stabilizing effect of the organotin compounds of the invention in the processing of polyvinyl chloride. The parts indicated are by weight.

100 Parts each of a suspension polyvinyl chloride having a K value of 68 were mixed with 0.4 part calcium stearate, 0.4 part hydrocarbon wax having a dropping point of about 90° C., and such an amount of the organotin stabilizer to be tested that always about the same tin content was present in the batch. For a comparison, known tin stabilizers were tested under the same conditions.

For determining the dynamic thermostability, the mixtures were applied to a laboratory two-roll mill heated at 180° C., and laminated at 20 rpm to a rough sheet within one minute. In intervals of 5 minutes, samples were taken from the rough sheet and the color was compared with that of an internal color scale. The individual tests were carried out until the rough sheet had become dark brown to black.

In order to determine the static thermostability, a rough sheet was first manufactured from the mixtures according to the above operation mode, and laminated on the mill for a further 10 minutes at 180° C. Subsequently, test specimens having a thickness of about 0.5 mm and a diameter of 30 mm were cut from the sheet taken off the roll. The specimens were wrapped with an aluminum sheet and tempered at 180° C. in a drying cabinet with air circulation. In intervals of 10 minutes, a specimen each was removed and its color compared with the color scale.

The numbers of the color scale used represent:
1 = transparent
2 = slightly yellowish
3 = distinct yellow color
4 = dark yellow to brown
5 = dark brown to black.

The test conditions and the results are listed in Tables 3 and 4. As results from the Tables, the novel stabilizers, at identical amounts of tin in the formulation and corresponding residues, have a PVC-stabilizing action comparable with that of known dibutyltin stabilizers (Examples 21 to 24 and 32), but have less influence on the transparency.

TABLE 4

| | | | Static thermostability | | | | | | |
|---|---|---|---|---|---|---|---|---|---|
| | Organotin stabilizer | | discoloration of a rough sheet in drying cabinet at a tempering time of | | | | | | |
| | | | 10' | 20' | 30' | 40' | 50' | 60' | |
| Ex. No. | acc. to Example | Parts = g Sn | to color number | | | | | | |
| 26 | 1 | 1.15 0.130 | 1 | 2 | 2-3 | 3 | 3-4 | 5 | |
| 27 | 2 | 1.0 0.125 | 1 | 2 | 2 | 3 | 4 | 5 | |
| 28 | 3 | 1.25 0.123 | 1 | 2 | 2-3 | 3 | 3-4 | 5 | |
| 29 | 5 | 1.5 0.125 | 1 | 2 | 3 | 3-4 | 4 | 5 | |
| 30 | 9 | 1.1 0.127 | 1 | 2 | 2 | 3 | 4 | 5 | |
| 31 | 10 | 1.45 0.131 | 1 | 2 | 2 | 3 | 3-4 | 5 | |
| 32 | Comparative substance di-butyltin-bis-2-ethyl-hexylthio-glycolate | 0.70 0.130 | 1 | 2 | 3 | 4 | 5 | | |

What is claimed is:
1. Mixture of organotin compounds having the formula

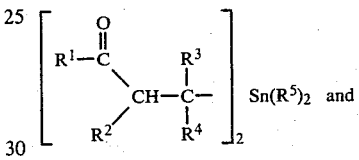

I

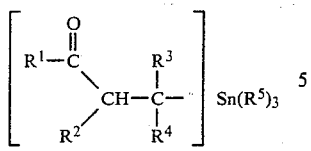

II in which
R¹ is OH, —NH₂, an alkylamino or arylamino, O-alkyl or O-aryl, both the latter two being unsubstituted or substituted by aryl or alkyl said aryl or alkyl being unsubstituted or substituted by a member selected from the group consisting of halogen, hydroxy, thioether, ether, and carboxyl;

R² to R⁴ are identical or different and each are
(a) 0 to 2 hydrogen atoms, or
(b) alkyl having from 1 to 30 carbon atoms, with the proviso that at least one is a

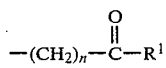

group, where R¹ is as defined above and n an integer of from 1 to 15;

R⁵ is —S—(CH₂)m—CO₂—alkyl, —S—alkyl, —O₂C—alkyl or —O₂C—CH=CH—CO₂—alkyl, m being 1 or 2 and the alkyl optionally contains —O—, —S— or —CO₂ groups and OH substituents;

and the R¹ to R⁵ corresponding to one another in the components I and II of the mixture always being identical.

2. Mixture of organotin compounds as claimed in claim 1, wherein in both components the radical R¹ is O-alkyl having from 1 to 30 carbon atoms, the radical R² is

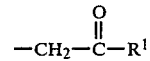

the radicals R³ and R⁴ each are hydrogen.

3. Mixture of organotin compounds as claimed in claim 1, wherein the weight ratio of component I to component II is from about 1:0.01 to 1:4.

4. A method of stabilizing halogen-containing polymers comprising mixing said polymers with the organotin compounds according to claim 1 in amounts of from 0.1 to 10 parts by weight per 100 parts by weight of polymer.

5. Plastics molding compositions comprising chlorine-containing polymers which contain organotin compounds according to claim 1 in amounts of from 0.1 to 10 parts by weight per 100 parts by weight of polymer.

* * * * *